(12) United States Patent
Schanen et al.

(10) Patent No.: US 8,633,334 B2
(45) Date of Patent: Jan. 21, 2014

(54) METHOD FOR PREPARING TRIFLUOROMETHANESULPHINIC ACID

(75) Inventors: Vincent Schanen, Lyons (FR); Olivier Buisine, Saint Genis Laval (FR); François Metz, Irigny (FR); Bernard Besson, Les Echets (FR)

(73) Assignee: Rhodia Operations, Aubervilliers (FR)

( * ) Notice: Subject to any disclaimer, the term of this patent is extended or adjusted under 35 U.S.C. 154(b) by 757 days.

(21) Appl. No.: 12/744,875

(22) PCT Filed: Nov. 25, 2008

(86) PCT No.: PCT/EP2008/066161
§ 371 (c)(1),
(2), (4) Date: Oct. 26, 2010

(87) PCT Pub. No.: WO2009/068533
PCT Pub. Date: Jun. 4, 2009

(65) Prior Publication Data
US 2012/0197039 A1    Aug. 2, 2012

(30) Foreign Application Priority Data
Nov. 27, 2007    (FR) ...................................... 07 08281

(51) Int. Cl.
*C07C 313/04*    (2006.01)
(52) U.S. Cl.
USPC .......................................... 562/125; 562/113
(58) Field of Classification Search
USPC ................................. 562/113, 125
See application file for complete search history.

(56) References Cited

U.S. PATENT DOCUMENTS 6,770,776 B2 * 8/2004 Janin et al. ..................... 560/153
2001/0031891 A1    10/2001 Goto et al.

FOREIGN PATENT DOCUMENTS

EP    0735023 A1    10/1996
WO    0149659        7/2001

OTHER PUBLICATIONS

Harzdorf, et al.; Über Perfluralkansulfinsäuren; Liebigs Annalen Der Chemie, No. 1, Feb. 22, 1973, pp. 33-39, XP002491378.

* cited by examiner

*Primary Examiner* — Peter G O Sullivan
(74) *Attorney, Agent, or Firm* — Hunton & Williams LLP

(57) ABSTRACT

The present invention relates to a method for preparing a highly pure trifluoromethanesulphinic acid. The method of the invention for preparing a highly pure trifluoromethanesulphinic acid, starting from an aqueous mixture comprising a trifluoromethanesulphinic acid salt, a trifluoroacetic acid salt and saline impurities resulting from the method for preparing same, is characterized in that said mixture is subjected to the following operations: —acidification such that the trifluoroacetic acid salt and the triflinic acid salt are released in an acid form, —separation of the trifluoroacetic acid and trifluoromethanesulphinic acid by distillation enabling the trifluoroacetic acid to be recovered at the top of the distillation and the trifluoromethanesulphinic acid to be recovered at the bottom of the distillation, —separation by distillation of the trifluoromethanesulphinic acid present in the distillation residue previously obtained.

19 Claims, No Drawings

METHOD FOR PREPARING TRIFLUOROMETHANESULPHINIC ACID

CROSS-REFERENCE TO RELATED APPLICATIONS

This application is the U.S. National Phase of International Application Number PCT/EP2008/066161 filed on Nov. 25, 2008, which claims priority to French Application No. FR 07/08281, filed Nov. 27, 2007, each of which is incorporated by reference herein in its entirety.

A subject matter of the present invention is a process for the preparation of trifluoromethanesulfinic acid.

The invention is targeted at the preparation of a trifluoromethanesulfinic acid of high purity.

Trifluoromethanesulfinic acid, commonly known as "triflinic acid", or else its salified forms are products used in numerous fields (plant protection, pharmaceutical or other).

One of the routes for the synthesis of said acid described in EP 0 735 023 consists in reacting trifluoroacetic acid, at least partially salified by an organic or inorganic cation, with sulfur dioxide in a polar organic solvent and heating the resulting mixture at a temperature of between 100° C. and 200° C. for a period of time of between 30 min and 20 hours.

The relative amounts of the trifluoroacetic acid and of the sulfur dioxide are such that the ratio of the number of sulfur atoms per mole of trifluoroacetic acid is between 1 and 10, advantageously in the vicinity of two.

At the end of the reaction, trifluoroacetic acid, trifluoromethanesulfinic acid in the saline form, preferably in the form of an alkali metal salt, preferably the sodium or potassium salt, and the organic solvent are obtained.

Fluoride or sulfate salts, generally in the form of salt of an alkali metal, preferably the sodium or potassium salt, are also coproduced during the reaction. These salts formed are known as "saline impurities" in the continuation of the present text.

Dilution is subsequently carried out by addition of water and then the polar organic solvent is extracted with an appropriate organic solvent, for example a chlorinated aliphatic hydrocarbon.

The organic and aqueous phases are separated.

An aqueous solution is generally obtained having a solids content of 10 to 40% by weight comprising:
  from 5 to 35% by weight of a trifluoromethanesulfinic acid salt, preferably an alkali metal salt,
  from 5 to 35% by weight of a trifluoroacetic acid salt, preferably an alkali metal salt,
  from 0.5 to 2% by weight of saline impurities.

Said aqueous solution preferably comprises from 15 to 20% by weight of a trifluoromethanesulfinic acid salt, from 10 to 15% by weight of a trifluoroacetic acid salt and from 0.5 to 2% by weight of saline impurities.

The object of the present invention is to provide a trifluoromethanesulfinic acid of high purity starting from an aqueous phase comprising a trifluoromethanesulfinic acid salt in combination with a trifluoroacetic acid salt and saline impurities resulting from its process of preparation.

The term "high purity" is understood to mean, in the present text, a trifluoromethanesulfinic acid having a purity of greater than or equal to 95%, preferably of greater than or equal to 98% and more preferably of greater than or equal to 99%.

Thus, a subject matter of the present invention is a process for the preparation of a trifluoromethanesulfinic acid of high purity starting from an aqueous mixture comprising a trifluoromethanesulfinic acid salt, a trifluoroacetic acid salt and saline impurities resulting from its process of preparation, characterized in that said mixture is subjected to the following operations:
  acidification in such a way that the salts of the trifluoroacetic acid and of the triflinic acid are released in an acid form,
  separation of the trifluoroacetic acid and the trifluoromethanesulfinic acid by distillation, making it possible to recover the trifluoroacetic acid at the distillation top and the trifluoromethanesulfinic acid at the distillation bottom,
  separation, by distillation, of the trifluoromethanesulfinic acid present in the distillation concentrate obtained above.

In the continuation of the account of the invention, trifluoromethanesulfinic acid is denoted "triflinic acid".

The process of the invention is based on the fact that an acidification is carried out in such a way that the salts of the trifluoroacetic acid and of the triflinic acid are released in an acid form and then that said acids obtained are separated by distillation.

According to a preferred alternative form of the process of the invention, the aqueous mixture collected is subjected to a concentration operation.

Specifically, it is desirable to concentrate said aqueous mixture before the acidification operation.

To this end, the aqueous mixture defined above can be concentrated so as to increase the concentration, of the salts of the trifluoroacetic acid and the triflinic acid in such a way that between 2 and 60% by weight, preferably between 5 and 50% by weight, of water is present in the concentrated solution obtained.

One embodiment for concentrating the reaction medium consists in carrying out the distillation of a portion of the water in order to achieve, in the reaction medium, the desired concentration of water.

The distillation can be carried out at atmospheric pressure at a temperature of 100° C.

The distillation can also be carried out under a pressure slightly lower than atmospheric pressure, for example of between 1 mbar and 600 mbar, and at a temperature of less than 100° C. Generally, the pressure is chosen in order to have a distillation temperature lying between 40° C. and 90° C.

Another embodiment consists in carrying out an entrainment by injection of a fluid, for example steam or inert gas, in particular nitrogen.

From a practical viewpoint, the concentration operations as well as the distillation operations described below can be carried out in an evaporator.

Use may be made of those which are available commercially and mention may be made, inter alia, of wiped film evaporators or falling film evaporators of Luwa® type.

The invention does not rule out the use of other concentration techniques, such as ultrafiltration or reverse osmosis.

In accordance with the process of the invention, an acidification of the concentrated aqueous solution is subsequently carried out.

The acidification is carried out using a strong acid having a $pK_a$ of less than or equal to 1.

The $pK_a$ is defined as the ionic dissociation constant of the acid/base pair when water is used as solvent.

The choice is made of a strong acid which advantageously does not exhibit an oxidizing nature. Thus, nitric acid is not preferred. More preferably, sulfuric acid, hydrochloric acid or phosphoric acid is resorted to.

Sulfuric acid is preferably chosen.

The amount of strong acid employed is such that the ratio of the number of moles of acid, expressed as H⁺ ions, to the number of moles of the salts of trifluoroacetic acid and of triflinic acid varies between 1 and 10, preferably between 1 and 4.

Advantageously, a concentrated solution of strong acid is resorted to.

Use is more particularly made of the commercial forms of acids.

Mention may in particular be made of 95 or 98% by weight sulfuric acid solutions, the 37% by weight hydrochloric acid solution or 95-100% by weight phosphoric acid solutions.

Use may also be made of hydrochloric acid in the gaseous form or of oleums, which correspond to sulfuric acid charged with sulfur trioxide $SO_3$, the concentration of which can vary between 10 and 60% by weight. Oleums comprising 20, 40 or 60% by weight of $SO_3$ are commercially available.

At the end of the acid treatment, an aqueous solution or suspension is collected which comprises the trifluoroacetic acid, the triflinic acid, the excess strong acid, the salts formed subsequent to the acidification and the acid forms corresponding to the saline impurities.

Generally, the solution or suspension obtained comprises from 4 to 26% by weight of trifluoroacetic acid, from 4 to 27% by weight of triflinic acid and from 5 to 60% by weight of water.

According to an alternative form of the invention, it is possible to add to the aqueous solution or suspension obtained, subsequent to the concentration but before the acidification, a compound capable of trapping hydrofluoric acid, for example boric acid or silica, for example at a content of 1% by weight.

Before carrying out the distillation of the trifluoroacetic acid, it is possible but not essential to carry out a separation of the solids present in the aqueous suspension (salts, silica, and the like) according to conventional solid/liquid separation techniques, preferably by filtration.

In a following stage, a distillation operation is carried out which makes it possible to bring about the separation of the trifluoroacetic acid and the triflinic acid.

The abovementioned aqueous phase comprising the acids to be separated is introduced into a distillation column and the trifluoroacetic acid and optionally water are removed at the distillation top and the triflinic acid, accompanied by the excess strong acid, the salts of the strong acids, in particular those originating from the acidification, and water, is recovered at the distillation bottom.

The distillation is carried out at a temperature in the reboiler of between 60° C. and 90° C. under a pressure ranging from 700 mbar to 50 mbar.

It is carried out in a conventional distillation apparatus.

A person skilled in the art is fully in a position to choose the means to be employed according to the compounds to be separated.

The following will simply be restated. The size (in particular the diameter) of the distillation columns depends on the circulating stream and on the internal pressure. They will thus be sized mainly according to the flow rate of mixture to be treated. The internal parameter which is the number of theoretical stages is determined in particular by the purity of the starting compound and the purity of the product which has to be obtained at the distillation top.

It will be specified that the columns can be packed without distinction with plates or with stacked packing, as is fully known to a person skilled in the art.

The plant being established, a person skilled in the art adjusts the operating parameters of the column.

Thus, the distillation column can advantageously but not limitingly be a column having the following specifications:
number of theoretical stages: from 1 to 10, preferably from 1 to 5,
reflux ratio R of between 1 and 20, preferably between 5 and 10.

A distillation concentrate, comprising the triflinic acid, is recovered at the column bottom and a gas phase, composed of the trifluoroacetic acid optionally accompanied by water, is recovered at the column top.

The gas phase is cooled and converted to the liquid form by cooling to a temperature, for example, of between −20° C. and 20° C., preferably of between −10° C. and 10° C.

This operation is carried out by passing through a condenser which is a conventional device, for example a tube heat exchanger fed with water or with a fluid maintained at a temperature in the vicinity of the cooling temperature chosen.

The choice is advantageously made, in carrying out the distillation operation, of equipment capable of withstanding the corrosion brought about by the compounds to be separated.

To this end, the choice is made of materials which are advantageously enameled steels.

The distillation concentrate comprising the triflinic acid which it is desired to obtain is subsequently treated.

To this end, the triflinic acid is distilled at a temperature which, for safety reasons, is maintained below 100° C., preferably below 90° C., under a reduced pressure preferably chosen below 50 mbar and more preferably between 0.1 mbar and 30 mbar. The choice is advantageously made of a pressure between 5 mbar and 30 mbar.

The invention does not rule out the addition of a third solvent in order to facilitate the distillation. Mention may in particular be made of aliphatic hydrocarbons, such as, for example, decane, decalin or petroleum fractions sold under the Isopar® name; aromatic hydrocarbons, such as in particular toluene, xylenes or mesitylene; halogenated aromatic hydrocarbons and very particularly monochlorobenzene, dichlorobenzene or their mixtures.

The amount of third solvent employed, expressed with respect to the weight present in the reboiler, can vary fairly widely. It can be equal, for example, to 10 to 100% by weight and preferably to 20 to 50% by weight.

The triflinic acid, optionally accompanied by the third solvent, is recovered at the distillation top and is liquefied by passing through a condenser maintained at a temperature of between −20° C. and 20° C.

A concentrate comprising residual triflinic acid, the salts of the strong acids, the excess strong acid used in the acidification, water and optionally the third solvent added is obtained at the distillation bottom.

The invention does not exclude the case where an additional distillation is carried out after the acidification operation which makes it possible to collect a mixture of the trifluoroacetic acid and the trifluoromethanesulfinic acid and then, starting from the mixture obtained of said acids, the separation of the trifluoroacetic acid and the trifluoromethanesulfinic acid is carried out, which separation is carried out as described above, namely a first distillation, which makes it possible to recover the trifluoroacetic acid at the distillation top and the trifluoromethanesulfinic acid at the distillation bottom, and then subsequently a second distillation of the distillation concentrate obtained above, which makes it possible to recover the expected trifluoromethanesulfinic acid at the distillation top.

In this alternative form, the distillation conditions which make it possible to recover the mixture of the trifluoroacetic acid and the trifluoromethanesulfinic acid are those defined for the recovery of the trifluoromethanesulfinic acid.

The process of the invention is highly advantageous as it results in triflinic acid with a high purity preferably of greater than or equal to 95%, more preferably of greater than or equal to 98% and more particularly of between 99 and 99.5%.

Implementational examples of the invention are given below by way of indication and without a limiting nature.

EXAMPLE 1

An aqueous solution (774 g) comprising 16% by weight of potassium trifluoromethanesulfinate and 13.5% by weight of potassium trifluoroacetate is charged to a 1 liter jacketed glass reactor equipped with a central stirrer and maintained under a nitrogen atmosphere.

The combination is placed under a pressure varying from 14 mbar to 2 mbar while maintaining a temperature of 50° C.

225 g of a suspension are obtained, which suspension remains fluid at 50° C.

The concentrated solution is run onto concentrated 92% sulfuric acid (780 g) in a reactor surmounted by a distillation column and by a condenser cooled with water (15° C.)

The temperature of the medium is kept below 30° C. during the operation in which the concentrated aqueous solution is run in.

The pressure is lowered to 280 mbar and the temperature of the reboiler is maintained at 68° C.

During the distillation, the pressure is gradually lowered to 86 mbar in order to maintain a satisfactory flow rate of distillate.

The first distillation fraction is collected (56 g) when the temperature of the vapors at the column top is between 26° C. and 36° C.

This fraction is composed of 85% by weight of trifluoroacetic acid and 15% of triflinic acid.

The pressure is subsequently lowered to 3 mbar.

A second fraction (44 g) is collected when the temperature of the vapors at the column top is between 29° C. and 41° C.

During this operation, the temperature of the reboiler varies from 70° C. to 79° C.

This fraction comprises 99% pure trifluoromethanesulfinic acid.

EXAMPLE 2

An aqueous solution (3000 g) comprising 16% by weight of potassium trifluoromethanesulfinate and 13.5% by weight of potassium trifluoroacetate is concentrated on a wiped film evaporator of Luwa type with an exchange surface area of 314 $cm^2$ maintained at a temperature of 80° C. and a pressure of 50 mbar.

The feed flow rate is adjusted so as to obtain 980 g of concentrated solution at the outlet of the evaporator.

The concentrated solution is run onto 2940 g of concentrated 96% sulfuric acid while maintaining the temperature below 20° C.

The pressure of the reactor is adjusted to 280 mbar and the temperature of the reaction mass is brought to 78° C.

A first fraction of 274 g is collected when the temperature at the column top is between 41° C. and 45° C.

The pressure is subsequently maintained at 1 mbar and a second fraction of 245 g is collected.

This fraction comprises 99% pure trifluoromethanesulfinic acid.

EXAMPLE 3

A mixture composed of potassium trifluoroacetate (84.0 g, 0.55 mol), potassium trifluoromethanesulfinate (93.4 g, 0.54 mol) and water (44 g, 2.4 mol) is added to phosphoric acid (600 g, 6.1 mol) brought to 60° C. and left stirring for one hour.

The medium is subsequently distilled under reduced pressure using a Vigreux column.

The temperature of the medium is brought to 70° C. under a reduced pressure of 150 mbar.

A fraction of 62.9 g having a boiling point of 24° C. at this pressure is thus obtained.

This fraction comprises 94% by weight of trifluoroacetic acid and 6% by weight of water.

The trifluoroacetic acid yield is 84%.

The temperature is subsequently raised to 90° C. and the pressure is lowered to 0.3 mbar.

71.1 g of a second distillation fraction having a boiling point of 28° C. are obtained.

This fraction comprises 79% by weight of trifluoromethanesulfinic acid and 21% by weight of trifluoroacetic acid.

The trifluoromethanesulfinic acid yield is 77%.

This fraction is redistilled under a pressure of 25 mbar.

A first fraction (16 g) comprising 94% by weight of water and a second fraction (47.8 g) comprising 98% by weight of trifluoromethanesulfinic acid are then obtained.

EXAMPLE 4

Concentrated 95% by weight sulfuric acid (162 g, 1.6 mol) is added to an aqueous solution (364 g) comprising potassium trifluoroacetate (95 g, 0.63 mol) and potassium trifluoromethanesulfinate (108 g, 0.63 mol) while maintaining the temperature of the medium below 10° C.

A solid is formed in the medium.

Stirring of the medium is maintained for 30 minutes and then the solid (205 g) is removed by filtration through a sintered glass funnel with a porosity of 3.

The filtrate obtained (301 g) is distilled under reduced pressure.

The medium is brought to a bulk temperature of 55° C. under a pressure of 18 mbar.

A first fraction (201 g) having a boiling point of approximately 25° C. is obtained.

This fraction comprises 27% by weight of trifluoroacetic acid and 73% by weight of water.

The trifluoroacetic acid yield is 77%.

The medium is subsequently brought to a temperature of 95° C. under a pressure of 0.2 mbar.

A second distillation fraction (57 g) comprising 72% by weight of trifluoromethanesulfinic acid and 28% by weight of water is obtained.

The trifluoromethanesulfinic acid yield is 64%.

This fraction is redistilled under a pressure of 25 mbar.

A first fraction (17 g) comprising 94% by weight of water and a second fraction (32 g) comprising 98% by weight of trifluoromethanesulfinic acid are then obtained.

What is claimed is:

1. A process for the preparation of a highly pure trifluoromethanesulfinic acid comprising:
   acidifying an aqueous mixture comprising a trifluoromethanesulfinic acid salt, a trifluoroacetic acid salt, and saline impurities, to convert the trifluoromethanesulfinic acid salt and the trifluoroacetic acid salt to acid form;
   distilling said aqueous mixture to separate the trifluoroacetic acid from the aqueous mixture and form a distillation concentrate comprising the trifluoromethanesulfinic acid; and distilling said distillation concentrate to obtain highly pure trifluoromethanesulfinic acid.

2. The process of claim 1, wherein the aqueous mixture is an aqueous solution comprising a solids content ranging from 10 to 40% by weight comprising:
from 5 to 35% by weight of the trifluoromethanesulfinic acid salt,
from 5 to 35% by weight of the trifluoroacetic acid salt, and
from 0.5 to 2% by weight of saline impurities.

3. The process of claim 1, wherein said aqueous solution comprises from 15 to 20% by weight of the trifluoromethanesulfinic acid salt, from 10 to 15% by weight of the trifluoroacetic acid salt, and from 0.5% to 2% by weight of saline impurities.

4. The process of claim 1, further comprising increasing the concentration of the trifluoroacetic acid salt and the trifluoromethanesulfinic acid salt in the aqueous mixture such that water is present in an amount ranging from 2 to 60% by weight in the concentrated aqueous mixture.

5. The process of claim 1, further comprising removing water by distillation at a pressure less than or equal to atmospheric pressure or by injection of a steam or an inert gas fluid.

6. The process of claim 1, wherein the acidifying step comprises adding a sulfuric, hydrochloric, or phosphoric acid, an oleum, or a gaseous hydrochloric acid to said aqueous mixture.

7. The process of claim 6, wherein the ratio of the number of moles of added strong acid, expressed as ions, to the number of moles of the salts of trifluoroacetic acid and of trifluoromethanesulfinic acid ranges from 1 to 10.

8. The process of claim 6, wherein a concentrated solution of strong acid added.

9. The process of claim 1, wherein the acidifying step yields an aqueous solution or suspension comprising the trifluoroacetic acid, the trifluoromethanesulfinic acid, excess strong acid, salts formed subsequent to the acidification, and the acid forms of the saline impurities.

10. The process of claim 9, wherein the acidifying step yields an aqueous solution or suspension comprising from 4 to 26% by weight of trifluoroacetic acid, from 4 to 27% by weight of trifluoromethanesulfinic acid, and from 5 to 60% by weight of water.

11. The process of claim 1, further comprising increasing the concentration of the trifluoroacetic acid salt and the trifluoromethanesulfinic acid salt in the aqueous mixture and subsequently adding a compound capable of trapping hydrofluoric acid to the aqueous mixture prior to the acidifying step.

12. The process of claim 1, wherein the aqueous phase obtained subsequent to the acidifying step is distilled such that the trifluoroacetic acid and optionally water is recoverable at a distillation top, and the trifluoromethanesulfinic acid, excess strong acids, salts of the strong acids, and water are recoverable from a distillation bottom.

13. The process of claim 12, wherein the distillation following the acidifying step is carried out at a temperature in a reboiler ranging from 60° C. to 90° C. under a pressure ranging from 700 mbar to 50 mbar.

14. The process of claim 12, wherein a gas phase comprising the trifluoroacetic acid and optionally water is cooled and converted to a liquid form by cooling to a temperature ranging from −20° C. to 20° C.

15. The process of claim 1, wherein the distillation concentrate comprising the trifluoromethanesulfinic acid is distilled so that the trifluoromethanesulfinic acid is recoverable at a distillation top, and a concentrate comprising residual trifluoromethanesulfinic acid, salts of strong acids, excess strong acid from the acidifying step, and water are recoverable at a distillation bottom.

16. The process of claim 15, wherein the trifluoromethanesulfinic acid in the distillation concentrate is distilled at a temperature below 100° C. under reduced pressure.

17. The process of claim 16, wherein a solvent comprising an aliphatic hydrocarbon, an aromatic hydrocarbon, a halogenated aromatic hydrocarbon, or a mixture thereof, is added to the distillation concentrate comprising the trifluoromethanesulfinic acid.

18. The process of claim 16, wherein the trifluoromethanesulfinic acid, and optionally a third solvent, is recovered at the distillation top and is liquefied by cooling to a temperature ranging from −20° C. to 20° C.

19. The process claim 1, wherein the highly pure trifluoromethanesulfinic acid has a purity of greater than or equal to 95%.

* * * * *

UNITED STATES PATENT AND TRADEMARK OFFICE
CERTIFICATE OF CORRECTION

PATENT NO.       : 8,633,334 B2               Page 1 of 1
APPLICATION NO.  : 12/744875
DATED            : January 21, 2014
INVENTOR(S)      : Schanen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 910 days.

Signed and Sealed this
Twenty-second Day of September, 2015

Michelle K. Lee
*Director of the United States Patent and Trademark Office*